United States Patent
Littmann et al.

(10) Patent No.: US 8,749,233 B2
(45) Date of Patent: Jun. 10, 2014

(54) METHOD AND MAGNETIC RESONANCE SYSTEM FOR COMBINING SIGNALS ACQUIRED FROM DIFFERENT ACQUISITION COILS

(75) Inventors: Arne Littmann, Erlangen (DE); Davide Piccini, Zane (VI) (IT); Michael Zenge, Nuremberg (DE)

(73) Assignee: Siemens Aktiengesellschaft, Munich (DE)

(*) Notice: Subject to any disclaimer, the term of this patent is extended or adjusted under 35 U.S.C. 154(b) by 347 days.

(21) Appl. No.: 13/289,309

(22) Filed: Nov. 4, 2011

(65) Prior Publication Data

US 2012/0112751 A1 May 10, 2012

(30) Foreign Application Priority Data

Nov. 4, 2010 (DE) .......................... 10 2010 043 370

(51) Int. Cl.
*G01V 3/00* (2006.01)

(52) U.S. Cl.
USPC .......................................................... 324/307

(58) Field of Classification Search
USPC ................................................. 324/300–322
See application file for complete search history.

(56) References Cited

U.S. PATENT DOCUMENTS

| | | | |
|---|---|---|---|
| 6,326,786 B1 | 12/2001 | Pruessmann et al. | |
| 6,486,671 B1 | 11/2002 | King | |
| 6,522,140 B2 * | 2/2003 | Harvey | 324/307 |
| 7,005,853 B2 * | 2/2006 | Tsao et al. | 324/309 |
| 7,309,985 B2 * | 12/2007 | Eggers et al. | 324/309 |
| 7,498,809 B2 * | 3/2009 | Takahashi et al. | 324/309 |
| 7,808,241 B2 * | 10/2010 | Dohata et al. | 324/318 |
| 8,274,284 B2 * | 9/2012 | Edelman et al. | 324/309 |
| 8,581,589 B2 * | 11/2013 | Wald et al. | 324/322 |
| 2004/0135579 A1 | 7/2004 | Takizawa et al. | |
| 2005/0237059 A1 | 10/2005 | Reykowski | |

FOREIGN PATENT DOCUMENTS

| | | |
|---|---|---|
| JP | 2006130285 A | 5/2006 |
| JP | 2009022319 A | 2/2009 |
| WO | WO 0208778 A1 * | 1/2002 |

OTHER PUBLICATIONS

"Mode Matrix—A Generalized Signal Combiner for Parallel Imaging Arrays," Reykowski et al., Proc. Intl. Soc. Mag. Reson. Med., vol. 11 (2004) p. 1587.
"A Dual-Projection Respiratory Self-Gating Technique for Whole-Heart Coronary MRA," Lai et al., Journal of Magnetic Resonance Imaging, vol. 28 (2008), pp. 612-620.
Free-Breathing Whole-Heart Coronary MRA With 3D Radial SSFP and Self-Navigated Image Reconstruction, Stehning et al., Magnetic Resonance in Medicine, vol. 54 (2005) pp. 476-480.

* cited by examiner

*Primary Examiner* — Dixomara Vargas
(74) *Attorney, Agent, or Firm* — Schiff Hardin LLP

(57) ABSTRACT

In a method and magnetic resonance (MR) apparatus for combining MR signals that were acquired with different acquisition coils from a region of an examination subject at least two MR signals that are based on MR signals acquired with at least two different acquisition coils are provided to a processor. Due to the spatially differing arrangement of the respective acquisition coils, the at least two MR signals image the region of the examination subject with different sensitivity profiles. The provided MR signals are combined, such that unwanted MR signal portions are suppressed, to form a combined MR signal with the suppression of unwanted MR signal portions being implemented by MR signal portions that were acquired with an acquisition coil that detects the unwanted MR signal portions with increased sensitivity in comparison to other acquisition coils being weighted less in the combined MR signal than other MR signal portions.

19 Claims, 7 Drawing Sheets

FIG 8
A)
B)
 ↑z
FIG 9
A)
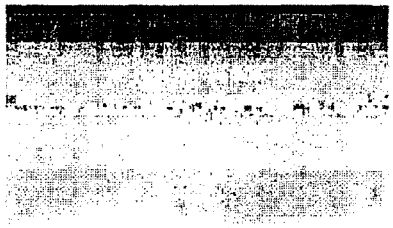
B)
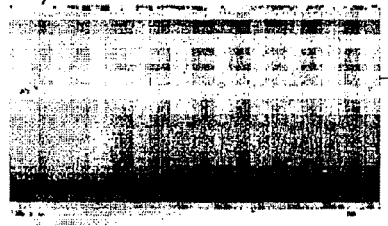 ~91
~92
z↑ 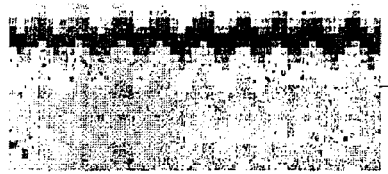 ~93
→t FIG 10
FIG 11
A)
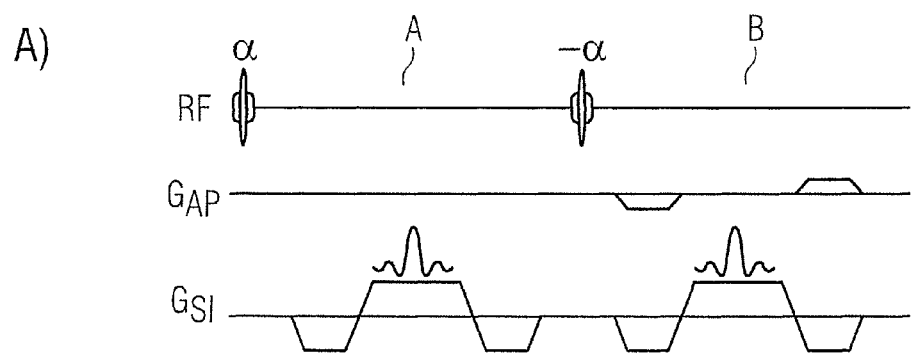
B)
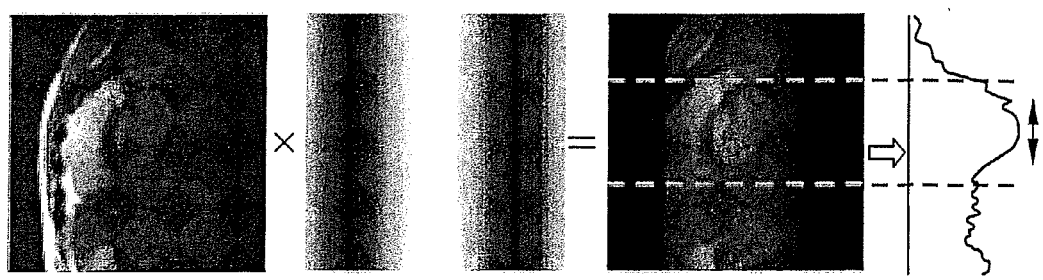

METHOD AND MAGNETIC RESONANCE SYSTEM FOR COMBINING SIGNALS ACQUIRED FROM DIFFERENT ACQUISITION COILS

BACKGROUND OF THE INVENTION

1. Field of the Invention

The present invention concerns a method for combination of magnetic resonance (MR) signals that were acquired with different acquisition coils from a region of an examination subject, as well as a magnetic resonance system for implementation of such a method.

2. Description of the Prior Art

Magnetic resonance tomography (MRT) is an imaging modality that enables the imaging of structures inside an examination subject (in particular even of soft tissues) with high resolution. In MRT, protons in the examination subject are aligned in a basic magnetic field (B0) so that a macroscopic magnetization arises that is subsequently excited by means of one or more induction coils, and a spatial coding of the acquired signal is achieved by the switching (activation) of slice selection, phase coding and/or frequency coding gradients before or during the signal/data acquisition. The induction signal acquired with an acquisition coil is subsequently demodulated with a reference signal, namely, a phase-shifted reference signal (quadrature detection) so that a complex MR signal is obtained that contains both magnitudes and phase information. Image data (in image space) are obtained by Fourier transformation of the MR signal (which exists in what is known as k-space).

To improve the signal-to-noise ratio (SNR), it is known to detect the MR signals with multiple coils of a coil array. A receiver may be provided for each coil, which results in the signal noise for the different coils not being correlated. The MR signals acquired with the different coils are subsequently combined so that the region to be shown is irradiated and detected as homogeneously as possible.

The occurrence of artifacts in the image data and the imaging of unwanted structures of the examination subject pose problems in MR imaging. For example, it is often desirable to not completely scan k-space in order to accelerate the acquisition of the image data. The region shown without artifacts— i.e. the field of view—is smaller due to this undersampling. Particularly for subjects of large dimensions, MR decay signals from outside of the field of view are also unavoidably detected. Upon a reconstruction of the image data, this leads to artifacts known as aliasing artifacts, since regions outside of the field of view are aliased in (folded into) the field of view. Such aliasing artifacts can be removed from the image data only with difficulty.

An additional example is the acquisition of image data of the heart with MRT. A correction for the intrinsic heart motion and for the gross motion of the heart due to breathing of the examined person should optimally take place. While the contraction of the heart can be detected by means of an EKG triggering, a technique known as "navigator gating" or "self-gating"—i.e. a self-triggering—in which the motion of the heart is derived from the acquired image data, is possible for the breathing correction. For example, given a radial scanning of k-space, the information that is contained in each radial projection along the SI (Superior-Inferior) direction is used to determine the heart movement. In general, an SSFP (Steady State Free Precession) sequence with large flip angles for the data acquisition is selected for such acquisitions in order to amplify the bright signal that stems from the accumulation of blood in the heart. However, external structures—for example arms, chest wall and spinal column—can similarly cause bright MR signals that are acquired during the measurement and contribute to the SI projection. A robust, one-dimensional segmentation of the heart is thereby hindered and precise navigation—based on a cross-correlation of two projections, for example—is thereby significantly hindered.

In order to avoid the acquisition of signals of interfering structures, a method described by C. Stehning et. al., "Free-Breathing Whole-Heart Coronary MRA with 3D Radial SSFP and Self-Navigated Image Reconstruction", Mag. Reson. Med. 54:476-480 (2005), is proposed. A slice-selective acquisition is implemented and regionally saturated slices (REST) are placed over structures that should not be imaged. The method shows good results for a Cartesian k-space scanning, but the use of a radial scan leads to a series of problems that are comparable to a filtering effect (in which there is an interaction between the sharpness of edges of the selected slice and the amplitude and number of oscillations beyond the passband). Moreover, the applicability of the method for the suppression of the imaging of multiple unwanted structures is reduced since each structure requires a separate saturated slice. Moreover, if the unwanted signal originates from structures that lie outside of the field of view (FoV), the positioning of saturation slices is very complicated or even impossible.

Furthermore, a solution that likewise concerns a breath triggering based on acquired MR signals is proposed by P. Lai et al. in "A Dual-Projection Respiratory Self-Gating Technique for Whole-Heart Coronary MRA", J. Magn. Reson. Imaging, 28:612-620 (2008). In order to suppress the acquisition of signals of the chest wall, a sinusoidal magnitude modulation is used that is perpendicular to the SI projection that is evaluated for the self-triggering. A Cartesian, volumetric, coronary imaging described as being used. In the method, two successively acquired SI projections are combined, with an additional gradient that is oriented in the anterior-posterior (AP) direction being additionally switched during the acquisition of the second projection. The parameters of the additional gradients (in particular duration and amplitude) can be selected by the operator according to the position of the heart within the desired field of view. This described solution is limited to this specific application and cannot be implemented in a three-dimensional radial imaging.

It is thus desirable to implement imaging of the above type such that only the anatomical structures to be shown in the image data are imaged and contributions of unwanted structures are suppressed. Moreover, such a method should have a high degree of effectiveness for the respective application. Such a method should also be flexibly applicable and in a multitude of situations. Furthermore, it is desirable to reduce the aliasing artifacts described above.

SUMMARY OF THE INVENTION

It is an object of the present invention to reduce at least some of the disadvantages cited in the preceding, and in particular to avoid the imaging of unwanted structures and/or of aliasing artifacts.

According to one aspect of the present invention, a method is provided for combining magnetic resonance (MR) signals that were acquired with different acquisition coils from a region of an examination subject. The method includes providing a computerized processor with at least two MR signals that are based on MR coil signals acquired with at least two different acquisition coils, wherein an "MR signal" means to the MR coil signals detected with one of the acquisition coils or a combination of MR coil signals detected with different individual acquisition coils. Due to the spatially differing location of the individual acquisition coils, the at least two MR signals image the region of the examination subject with different sensitivity profiles. The provided MR signals are combined such that unwanted MR signal portions are suppressed. A combined MR signal is thereby formed. Based on the spatial arrangement, one of the acquisition coils can (will) detect the unwanted MR signal portions with higher sensitivity than another of the acquisition coils. The unwanted MR signal portions are now suppressed by MR signal portions (components or contributions) that were acquired with higher sensitivity by such an acquisition coil being weighted less than other MR signal portions in the combined MR signal.

The locally different sensitivities of the respective acquisition coils thus can be utilized in order to suppress the unwanted MR signal portions. In contrast to conventional methods, no optimally homogeneous irradiation/detection is thus sought; rather, specific MR coil signals are deliberately given less consideration than others.

The term MR signal as used herein encompasses and possibly combines MR coil signals, namely the signals acquired in order to scan k-space (k-space data), or signals transformed into the image domain (image data). The combination of the MR signals thus can take place analogously after the acquisition, but also by a combination of k-space data or a combination of image data.

The provided MR signals can be complex (i.e. have real and imaginary signal parts) so that a complex combined MR signal is obtained. However, it is also possible to combine only the magnitudes of the MR signals. For example, by suppressing the unwanted MR signal portions, aliasing artifacts can be reduced or unwanted structures can be imaged with lower contrast, or their imaging can be completely suppressed.

In an embodiment of the invention, the combining of the MR signals includes weighting of the MR signals with a respective weighting factor. Furthermore, this embodiment of the method can include an adaptation of the weighting factors so that the unwanted MR signal portions are minimized in the combined MR signal. The influence of the unwanted MR signal portions on the combined MR signal thus can be further reduced. For example, a numerical optimization method that minimizes the unwanted signal portions can be used to determine the weighting factors.

Furthermore, the method can include specification of a region of the examination subject that is to be shown in positional or image space, with the unwanted signal portions then being those that were acquired by the at least two acquisition coils from outside the region to be shown. For example, the region to be shown can be the field of view (FOV), or it can be a structure of the examination subject that is to be shown. The MR signals can then be combined such that MR signal portions that were acquired with an acquisition coil that detects the MR signal portions from outside of the examination subject with increased sensitivity in comparison to other acquisition coils are weighted less in the combined MR signal than other MR signal portions. The specification of the region can take place manually or automatically. Upon scanning of k-space, for example, the corresponding region—and therefore the combination of the MR signals—can be established according to the FOV that is thereby provided.

The unwanted signal portions can be caused by structures of the examination subject whose imaging should be suppressed and/or can be those MR signal portions that were acquired from outside of a field of view to be shown.

The MR signals can be provided and combined in analog form, but it is also possible to provide and combine the MR signals in digital form. For example, digital MR signals can be obtained by an analog-to-digital conversion (ADC) of the MR coil signals or of combined MR coil signals that is part of the processing. Naturally, the MR coil signals can be provided t the processor already in digital form.

The at least two MR signals can also be provided and combined in the form of at least two MR image data sets (data files). One MR image data set can then be acquired with one of the acquisition coils and correspond to MR coil signals transformed into image space, or correspond to a combination of MR coil signals acquired with various individual coils that is transformed into image space. For example, magnitude images corresponding to the MR signals can thus be combined in a simple manner in image space.

In one embodiment, at least one of the provided MR signals is an MR mode signal that corresponds to a combination of MR coil signals detected with different individual acquisition coils. The method can furthermore comprise the formation of the MR mode signal from the corresponding MR coil signals. "Mode signal" here is merely used as a name for a combination of MR coil signals. For example, the use of such mode signals can be reasonable in order to reduce the number of channels to be processed. The MR coil signals can be provided in analog form and be combined to form the mode signal, for example by means of a hardware component configured for this. However, the MR coil signals can also be provided in digital form and be digitally combined to form the MR mode signal. For example, this can take place by means of corresponding software instructions or in a digital module (chip, DSP for example) configured for this purpose.

It is likewise possible for all of the MR signals to be combined to be MR mode signals (for example MR mode signals transformed into image space). For example, the mode signals can be generated with a hardware component and subsequently be processed further with a software component to form the combined MR signal.

For example, an MR mode signal can be a linear combination of at least two MR coil signals that are respectively weighted with a real and/or imaginary weighting factor. Such a linear combination can be achieved with what is known as the "mode matrix", for example.

In another embodiment, the method furthermore includes the provision of the MR coil signals acquired with the at least two acquisition coils and the implementation of a principal component analysis of the at least two coil signals to determine linearly independent principal components of the MR coil signals. Particularly in the case of larger coil arrays, correlations of the MR coil signals acquired with adjacent coils can occur, such that the determination of the linearly independent principal components for such a signal matrix is advantageous. The MR coil signals can then be combined such that at least two linearly independent MR mode signals are formed that correspond to the principal components in order to provide the at least two MR signals. The number of MR signals to be processed can therefore be reduced and, moreover, they are linearly independent, such that when combining the MR signals, an arbitrary weighting of the MR signal portions corresponding to the individual acquisition coils is enabled in principle. An effective suppression of the unwanted MR signal portions can thus be realized with reduced computing cost.

In an exemplary embodiment, the first provided MR signal corresponds to a first MR mode signal that was obtained via combination of the MR coil signals of a first outer coil (R), a second middle coil (M) and a third outer coil (L). For example, these can be arranged in a linear array. The combination of the coil signals takes place according to the equation $$\frac{1}{2}R$$

$$\frac{i}{\sqrt{2}}M$$

$$\frac{1}{2}L.$$

The second provided MR signal corresponds to a second MR mode signal that was obtained via combination of the MR coil signals of the first outer coil (R) and the third outer coil (L), according to the equation $$\frac{1}{\sqrt{2}}R + \frac{1}{\sqrt{2}}L.$$

The combined MR signal can then be formed by transforming the first and second mode signal into image space to provide the first or second MR signal, and subtracting the magnitude of the second MR signal from the magnitude of the first MR signal.

For example, given such a coil configuration the middle coil M can detect decay signals of a heart of an examined person with higher sensitivity than the outer coils R and L. These can in turn detect regions of the ribcage (whose imaging is unwanted) with increased sensitivity. MR signal portions of the coils R and L can accordingly be weighted less in the combined image data.

The at least two acquisition coils can be part of a coil array.

The method can furthermore include implementation of a reference measurement to acquire at least one first and one second MR coil signal with a first or a second of the at least two acquisition coils, a determination of the MR signals from the acquired MR coil signals, and a determination of a combination of the MR signals in which the unwanted MR signal portions are reduced. For example, the reference measurement can take place with a phantom. The determination of the combination of the MR signals can be the determination of combination parameters such as weighting factors, in particular factors of a linear combination of the MR signals. In subsequent measurements the combination parameters determined in such a manner can be applied for a suppression of the unwanted MR signal portions.

The method can furthermore include a repeated acquisition of the MR coil signals with the at least two acquisition coils to scan k-space, wherein k-space is scanned with a Cartesian or radial technique (trajectory); and the reconstruction of image data from the acquired k-space data to determine the first and second MR signals.

It is also possible to acquire only one k-space line (or a spoke in the case of a radial scan) so that the MR signals respectively correspond to a projection profile in image space. By using the combined MR signals in which the unwanted signal portions are suppressed, the imaging of unwanted structures can be suppressed in the reconstructed image data.

The method can include the acquisition of the MR coil signals with a projection measurement, wherein one-dimensional image data can be reconstructed from the MR coil signals or the combined MR coil signals to provide the MR signals. The combination of the MR signals (i.e. the one-dimensional image data) can take place such that structures that are not to be imaged are suppressed. The position of a structure (a heart, for example) can therefore be precisely determined from the combined one-dimensional image data. Since no interfering structures (the ribcage, for example) are imaged, such a position determination can also take place automatically.

The method can be implemented repeatedly in order to determine a time series of combined image data. In the time series of image data, the movement of the imaged structure can be determined by the position of the image structure of the examination subject being determined (detected) in the image data of the time series. A "self-gating"—i.e. of the type known as a self-triggering—can thus be realized. The time series delivers information about the movement of the imaged structure with which a movement correction can subsequently take place. K-space can be scanned radially, with a k-space line (along the z-axis, for example) being evaluated to determine the movement of the structure. This is possible in principle for each spoke of the radial scan, so the movement can be determined in corresponding directions without interfering structures. A robust, automatic evaluation of the data can take place via suppression of the imaging of unwanted structures.

According to a further aspect of the present invention, a magnetic resonance system is provided that is designed to combine MR signals that were acquired with different acquisition coils from a region of an examination subject. The magnetic resonance system has at least one first and second acquisition coil to detect at least one first or, respectively, second MR coil signal, wherein the at least two acquisition coils are arranged at different spatial positions. The magnetic resonance system furthermore comprises a processing unit that is configured to implement the following steps. At least two MR signals are received, wherein an MR signal corresponds to the MR signals detected with an acquisition coil or a combination of MR coil signals detected with different individual acquisition coils. The at least two MR signals image the region of the examination subject with different sensitivity profiles due to the spatially different arrangement of the acquisition coils; and combine the provided MR signals, such that unwanted MR signal portions are suppressed, to form a combined MR signal, The suppression of unwanted MR signal portions takes place such that MR signal portions that were acquired with one acquisition coil that detects the unwanted MR signal portions with increased sensitivity in comparison to other acquisition coils are weighted less in the combined MR signal than other MR signal portions. Advantages similar to those described in connection with the method can be achieved with the magnetic resonance system according to the invention.

The magnetic resonance system can be designed to implement any of the method embodiments described in the preceding. In particular, the computer (processing unit) can be configured in order to implement method steps described in the preceding. The magnetic resonance system can naturally include additional components. For example, hardware components can be provided for the combination of detected MR coil signals and/or for the combination of MR signals. Furthermore, a control unit can be provided that activates the magnetic resonance system to implement a defined imaging sequence (for example with a Cartesian or radial scanning of k-space) in order to acquire corresponding MR coil signals with the at least two acquisition coils.

The present invention also encompasses a non-transitory computer-readable data storage medium encoded with programming instructions (control commands) that, when the data storage medium is loaded into a computerized control system of a magnetic resonance imaging system, cause the computerized control system to operate the magnetic resonance system in accordance with one or more embodiments of the method described above.

Naturally, the features of the embodiments and aspects of the invention that are described in the preceding can be combined with one another. In particular, the features can be used not only in the described combinations but also in other combinations or independently, without leaving the scope of the invention.

BRIEF DESCRIPTION OF THE DRAWINGS

FIG. 8 illustrates acquired MR signals in the form of reconstructed image data that were determined in a conventional manner (A) or, respectively, according to an embodiment of the invention (B).

FIG. 9 illustrates MR signals in the form of one-dimensional reconstructed image data that were acquired with a projection measurement, wherein the MR signals were determined with a conventional method (A) or, respectively, according to an embodiment of the invention (B), and wherein the projections of 50 successive heart beats are shown.

FIG. 10 illustrates details of a radial 3D acquisition of a phantom with a sagittal slice selection with a method according to the prior art.

FIGS. 11A and 11B schematically illustrate a double projection breath triggering method according to the prior art.

DESCRIPTION OF THE PREFERRED EMBODIMENTS

Figure 1:
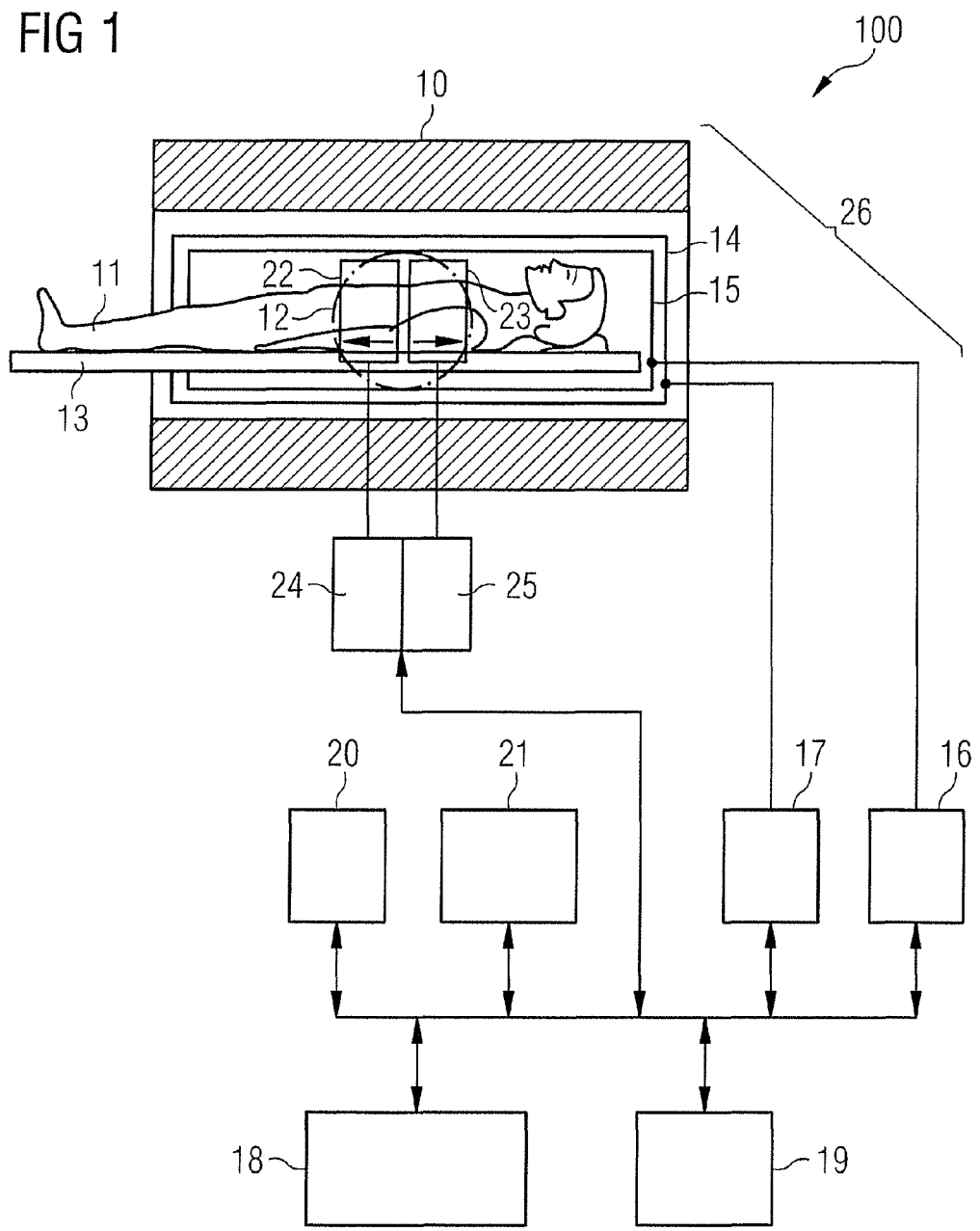
FIG. 1 is a schematic representation of a magnetic resonance system according to an embodiment of the present invention.

With the embodiments of the invention that are described in the following, it should be avoided that reconstructed MR image data depict unwanted structures or artifacts. In the prior art, the mapping of unwanted structures is achieved via the placement of regional saturation slices (REST) over these structures, for example, as is described in the publication by C. Stehning et. al., "Free-Breathing Whole-Heart Coronary MRA with 3D Radial SSFP and Self-Navigated Image Reconstruction", Mag. Reson. Med. 54:476-480 (2005). As an example, FIG. 10 illustrates a detail of a radial three-dimensional acquisition of a phantom with sagittal slice selection. The image in FIG. 10 shows how the suppression of an unwanted lateral signal with such a method leads to the situation that the image data represent a compromise between the sharpness of the edges at which the suppression is applied and the signal oscillations across the imaged subject. The edges of the subject at the right and left image edge where the presentation of the structure was suppressed are blurry, wherein the middle of the image in which the actual homogeneous phantom is imaged exhibits oscillations of the image intensity.

The method described by P. Lai et al. in "A Dual-Projection Respiratory Self-Gating Technique for Whole-Heart Coronary MRA", J. Magn. Reson. Imaging, 28:612-620 (2008) also has disadvantages in the avoidance of the presentation of unwanted structures. This method according to the prior art uses a sequence diagram that is schematically illustrated in FIG. 11A, in which an additional Anterior-Posterior (AP) gradient is switched at the second SI acquisition (reference character B). Reference character A identifies the first projection acquisition. FIG. 11B shows a graphical illustration of the method. The left image of FIG. 11b shows a central slice image that was reconstructed using exclusively the anterior acquisition coil. The second image represents a sinusoidal magnitude modulation in the AP direction. By adjusting the additional AP gradient, the dark and light fields can essentially be positioned in the anterior chest wall or, respectively, the heart. The combined projection thus primarily contains signals that originate from the heart of the examined person, wherein the imaging of the chest wall is suppressed. The region that depicts the heart is clarified by two dashed lines in the right image. A projection of the right image along these lines leads to the projection profile illustrated next to this, in which the heart is now clearly apparent. However, this method according to the prior art is limited to this specific application and can in particular not be implemented effectively for a three-dimensional radial imaging.

FIG. 1 schematically shows a magnetic resonance system 100 according to one embodiment of the present invention. The MR system 100 has a magnet 10 to generate a polarization field $B_0$. An examination subject 11 (here an examined person) can be shifted on a bed table 13 into the magnet 10, as is schematically represented by the arrow. The MR system furthermore has a gradient system 14 to generate magnetic field gradients that are used for the imaging and spatial coding. To excite the polarization resulting in the basic magnetic field, a radio-frequency coil arrangement 15 is provided that radiates a radio-frequency field into the examined person 11 in order to deflect the magnetization out of the steady state. A gradient unit 17 is provided to control the magnetic field gradients and an RF unit 16 is provided to control the radiated RF (radio-frequency) pulses.

The acquisition of magnetic resonance signals from the examination region 12 can take place by means of the radio-frequency coil arrangement 15. However, the magnetic resonance system can also have local acquisition coils or component coils. Two local acquisition coils 22 and 23 are illustrated as examples in FIG. 1. The MR system 100 can comprise additional acquisition coils; for example, 3 or more acquisition coils can be provided. The coils 22 and 23 can also be part of a larger coil array that, for example, has 16, 32 or more coils. MR system 100 can be designed to implement an accelerated acquisition method (for example GRAPPA, SENSE or SMASH) using the acquisition coils 22 and 23.

The acquisition coils of such a coil array can each have their own acquisition units (here the acquisition units 24 or, respectively, 25), such that an MR coil signal can be acquired in parallel with each acquisition coil. The respective coil noise thereby remains uncorrelated, such that a better SNR is achieved.

The acquisition coils 22 and 23 have sensitivity profiles that have different spatial arrangement. The sensitivity profile of the coil 22 across the examination region 12 is different than that of the coil 23. The coils are positioned such that their sensitivity at different positions is maximum. The acquisition coils thus detect RF signals predominantly from a region of the examination subject 11 in whose neighborhood they are arranged. RF signals from the region below coil 22 are detected only with lower sensitivity by coil 23, for example.

Due to the spatially different arrangement of the coils, and thus the different sensitivity profiles, additional spatial information is obtained that can be used (for example in accelerated acquisition methods) for the reconstruction of omitted k-space lines, or in the anti-aliasing (unfolding) of image data in image space.

The components of the magnetic resonance system that serve for the acquisition of MR data (for example the units 14-17 and 22-25) are designated together as an acquisition unit 26.

The magnetic resonance system is centrally controlled by the control/computer unit 18. Unit 18 controls the radiation of RF pulses and the detection of resulting RF signals. The magnetization excited given the decay of the magnetization excited in the examination region 11 induces an induction signal in the respective acquisition coil 22 or, respectively, 23, which induction signal is amplified (intensified) and demodulated by the respective acquisition unit 24 or, respectively, 25. The demodulation can take place in that the amplified induction signal is down-mixed with a reference signal and the reference signal phase-shifted by 90° into a band of audio frequencies. The two signals obtained in such a manner represent the real part and imaginary part of the output signal of an acquisition unit that is designated as an MR coil signal in the following. This is an example of a possibility of realizing a quadrature detection. Other known methods to generate a complex MR coil signal can naturally likewise be used in the MR system 100.

A frequency and/or phase coding can be implemented (by switching the corresponding gradients) so that the MR coil signal essentially corresponds to a k-space line. With multiple coding steps within the scope of an imaging sequence (controlled by control unit 18), k-space can be scanned by sequential acquisition of MR coil signals.

Processing unit 19 is designed (configured) to process acquired MR coil signals. For this purpose, an analog-to-digital conversion (ADC) of the MR coil signals can be implemented by processing unit 19 or a separate ADC unit (not shown). Processing unit 19 can then process the coil signals in digital form to form the combined MR signal, for example by executing corresponding control instructions at a microprocessor of the processing unit 19 that are stored in a memory of the unit 19.

Processing unit 19 can also be designed in order to implement the signal processing in analog form. Corresponding hardware or circuit components can be provided for this in unit 19, for example subtraction and/or addition circuits and the like. In particular, such components can be provided that implement a combination of multiple input signals via addition/subtraction of the input signals, advantageously with weighting of the additional input signals.

The processing unit 19 and the control/computer unit 18 can also be implemented as one unit, for example in the form of corresponding program steps that run on a microprocessor. Naturally, it is likewise possible to separately provide a control unit and a computer.

Individual MR coil signals can already have been combined before the processing, wherein a signal resulting from this is designated as an MR mode signal in the following. This has the advantage that the number of signals to be processed can already have been reduced beforehand, which in particular preserves resources of the processing unit 19 given larger coil arrays. The formation of the mode signals can in turn take place analogously by combination of analog MR coil signals, for example in a further processing unit with corresponding hardware or, respectively, circuit components (not shown). A combination of digital MR coil signals (after their ADC) to form the mode signals is also conceivable, wherein this can take place in processing unit 19 (via corresponding program instructions or hardware components such as DSPs) or an additional processing unit (not shown).

Furthermore, processing unit 19 can implement a transformation of the MR coil signals or MR mode signals in image space (also called positional space). An individual k-space line can be transformed (for example in a projection measurement), or k-space can initially be scanned via repeated acquisition of MR coils or, respectively, MR mode signals and a 2D- or 3D-transformation into image space can subsequently take place. Image data are thereby obtained.

The detected MR coil signals, the combined MR coil signals (MR mode signals) and the transformed MR coils or mode signals (image data) are herein collectively designated as MR signals. Processing unit 19 is designed for further processing of these MR signals, in particular for combination of MR signals with different sensitivity profiles to form the combined MR signal.

A pre-processing of the complex signals can take place, as well as a prior determination of the signal magnitudes and a combination of these. The procedure depends on the requirements of the respective application. For example, complex MR mode signals are determined and transformed, wherein then the magnitudes of the obtained complex image data are combined to form the combined MR signal.

The processing unit 19 combines the acquired MR signals such that the MR coil signals of specified acquisition coils are effectively weighted less than those of other acquisition coils in the resulting combined MR signal. These specific acquisition coils are those that acquire unwanted MR signal portions with increased sensitivity. Such unwanted signal portions can, for example, be MR signals of structures whose depiction should be suppressed, or MR signals from regions of the examination subject 11 that are situated outside of the field of view that should be imaged in the corresponding MR measurement. Due to the lower weighting, the unwanted MR signal portions can be suppressed in the combined MR signal so that the unwanted structures are shown with reduced intensity in the ultimately reconstructed image data, or so that aliasing artifacts are reduced, for example. Examples are subsequently described for various application cases with reference to Figures.

MR system 100 furthermore has an input unit 20 with which an operator can select a sequence protocol to acquire the MR coil signals and can input and modify imaging parameters that are displayed on a display 21.

The general functionality of an MR system is known to those skilled in the art, such that a more detailed description of the general components is not necessary herein.

Figure 2:
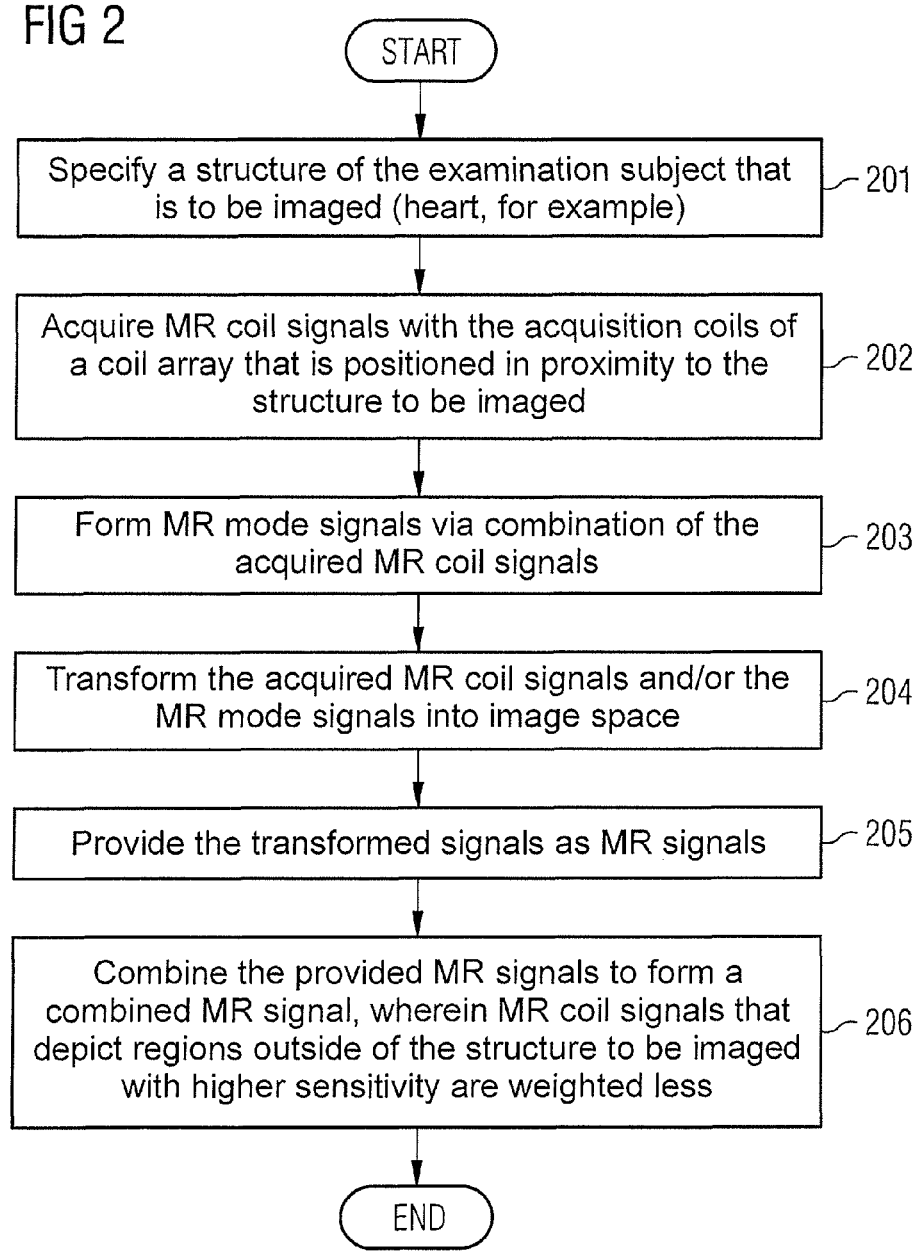
FIG. 2 is a flow chart that illustrates a method to combine MR signals according to an embodiment of the present invention.

An embodiment of the method according to the invention that can be executed at the magnetic resonance system 100 of FIG. 1 is illustrated in the flow chart of FIG. 2. The body part or volume and/or the position of a structure of the examination subject to be imaged initially takes place in Step 201. For example, this can take place by selection of a corresponding acquisition program by means of input unit 20. It is likewise conceivable to select a structure (an organ of the examined person 11, for example) from an anatomical atlas, or to implement an MRT overview measurement, wherein the structure to be imaged is selected in a corresponding image, for example via definition of a "Region of Interest" (ROI). This can in turn take place via user input by means of input unit 20.

In Step 202 MR coil signals are acquired with the acquisition coils of the acquisition unit 26, wherein the acquisition coils are positioned in proximity to the structure to be imaged (for example in proximity to the examined person 11) so that the acquisition coils detect RF signals of different regions of the examined person with different sensitivity.

The acquired MR coil signals can now be provided as MR signals, or can have been combined beforehand into MR mode signals (Step 203), wherein these mode signals are provided as MR signals. However, in both cases a transformation of the corresponding signals into image space can also furthermore take place (Step 204) in order to provide the transformed signals as MR signals (Step 205), as this is illustrated in FIG. 2. The MR mode signals can be determined as described in the preceding with reference to FIG. 1.

The use of MR coil signals or MR mode signals for continuative processing (suppression of unwanted signal portions) is in particular advantageous when the phase positions of the respective signals (i.e. of the different acquisition channels) are known so that the signals can be combined directly. The number of channels can thereby be reduced by using mode signals. If the phase positions are unknown, the previous transformation into image space and the combination of magnitudes is advantageous.

In Step 206 the provided MR signals are combined to form a combined MR signal. The combination now takes place such that MR coil signals that image regions outside of the predetermined structure to be imaged with higher sensitivity are weighted less than the remaining MR coil signals. Additional structures whose imaging would hinder a subsequent evaluation of image data (for example the segmentation of a one-dimensional projection) can be situated in regions outside of the structure to be imaged. The depiction of such structures in the image data is suppressed via the lower weighting. The MR signal combined in such a manner already exists in image space in the example of FIG. 2. If the MR signals are combined before the transformation into image space, the transformation into image space can take place in an additional step after 206.

The method of FIG. 2 describes an example of the determination of a combined MR signal that, for example, corresponds to a k-space line. It should be clear that a Cartesian or radial scanning of k-space can similarly be produced, for example, and in Step 204 two-dimensional or three-dimensional image data can be determined that are subsequently combined. Given a direct combination of coil or mode signals, this can take place for each scan step.

This is illustrated in an example in FIG. 8 for a two-dimensional scan of k-space. The left image (A) was reconstructed from k-space data that were acquired with a coronal Cartesian two-dimensional scan. In addition to the heart of the examined person, the image clearly shows additional organs such as the liver, as well as the ribcage and arms. The acquisition thereby took place with three acquisition coils whose coil signals were combined into an MR mode signal which represents the raw k-space data forming the basis of the image reconstruction.

In the example, the predetermined structure to be imaged is the heart of the examined person. For its presentation, in FIG. 8 (B) MR coil signals that image the aforementioned remaining structures with increased sensitivity were weighted less in the formation of the MR signal in order to suppress these structures. The formation of the combined MR signal is described in more detail in the following with reference to FIG. 5. This combined MR signal corresponds to the right MR image (B). The suppression of the unwanted structures (arms, ribcage, liver, etc.) via use of the combined MR signal according to one embodiment of the invention is clearly apparent via a comparison of the images (A) and (B). The heart is shown with essentially the same contrast.

Figure 3:
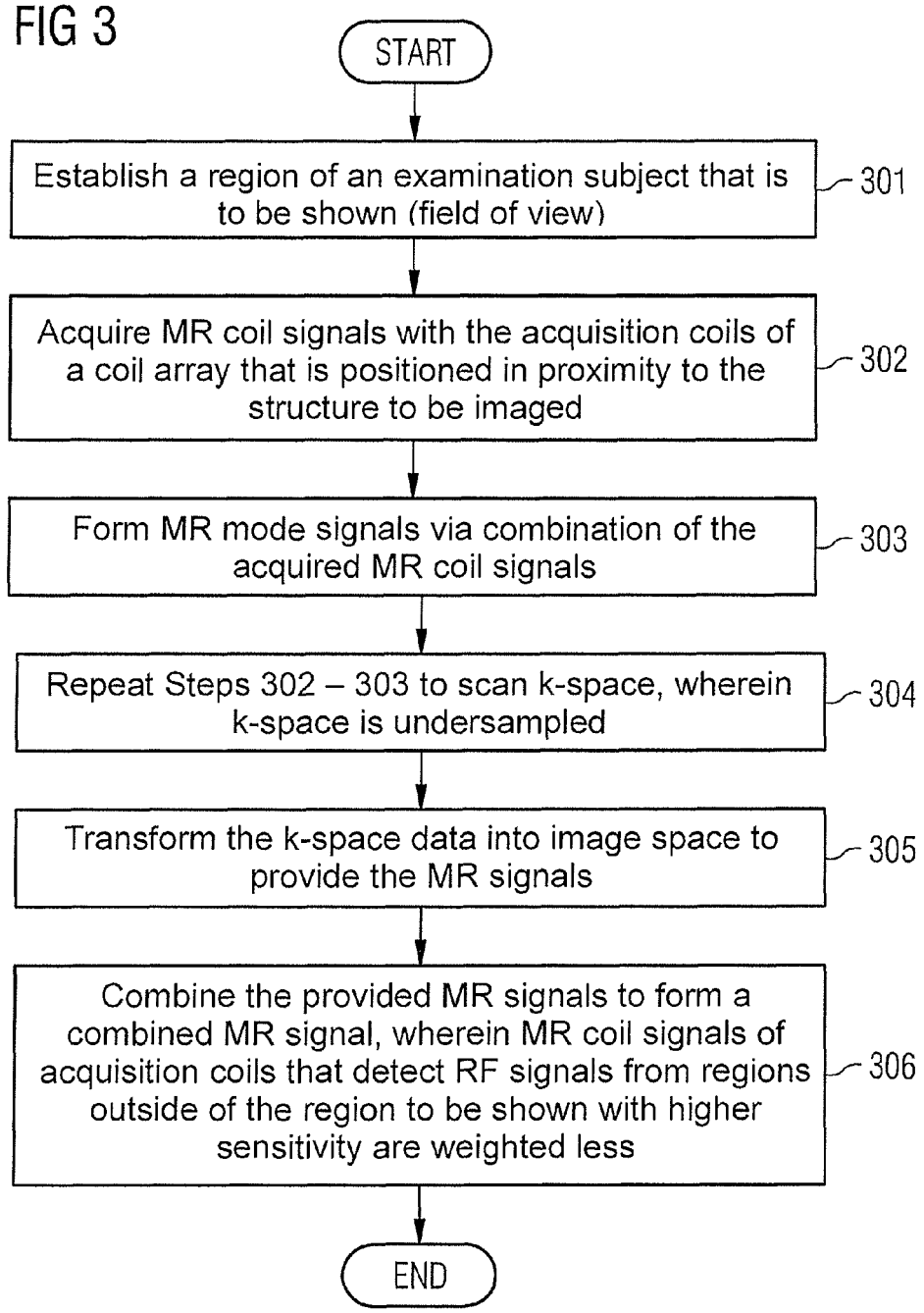
FIG. 3 is a flow chart that illustrates a method to combine MR signals according to a further embodiment of the present invention.

The flow diagram of FIG. 3 illustrates an additional embodiment of the method according to the invention that can in turn be executed by the MR system 100. The method serves to suppress aliasing artifacts. In a first Step 301, a region of an examination subject that is to be shown is established. The establishment of this field of view that should be imaged in the subsequent MR measurement can, for example, take place via determination of the density with which k-space is scanned. A lower scanning density (or sampling rate) corresponds to a smaller field of view. An undersampling can thereby occur since, due to the Nyquist criterion at a specific sampling rate, only spatial frequencies up to a defined upper limit can be acquired. Aliasings thereby occur that appear as aliasing artifacts in image space.

Another possibility for the establishment of the region of an examination subject that is to be shown is the selection of the region by means of the input unit 20, for example at an overview image of the examination subject that was acquired beforehand.

With an acquisition sequence corresponding to the field of view, MR coil signals are acquired in Step 302 with the acquisition coils (coils 22 and 23, for example) of a coil array. As before, the acquisition coils have different sensitivity profiles. The MR coil signals and/or MR mode signals determined from these (Step 303) are acquired repeatedly to scan k-space (Step 304). A transformation of the k-space data into image space and the provision of the corresponding image data as MR signals take place in Step 305. It should be clear that here, as in other exemplary embodiments, one image data set that—depending on the scan (Step 304) of k-space—comprises one-dimensional, two-dimensional or three-dimensional image data can also be determined per MR coil signal or, respectively, per MR mode signal.

The MR signals determined in such a manner are combined in Step 306 (in processing unit 19), wherein the combined MR signal is formed so that the aliasing artifacts are suppressed. This is achieved in that the MR coil signals of acquisition coils that detect RF signals from regions outside of the field of view to be shown with higher sensitivity are weighted less than other MR coil signals. The signal portions of such coils are thus weighted less in the combined MR signal. Since these coil signals image regions outside of the field of view to be shown, these coil signals can lead to aliasing artifacts, such that a lower weighting of these coil signals reduces the aliasing artifacts.

Since image data are combined in the example of FIG. 3, no additional processing steps are necessary. Given a combination of coil or, respectively, mode signals in Step 306, the combination can also already have taken place at each scan step, and a transformation into image space can be conducted after Step 306.

Figure 4:
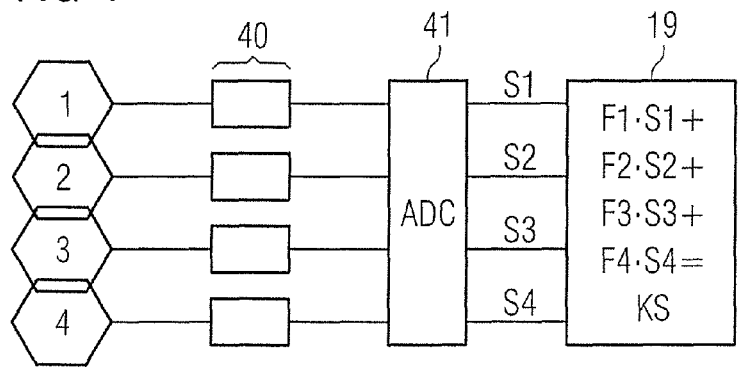
FIG. 4 schematically illustrates the combination of MR signals that correspond to MR coil signals acquired with different acquisition coils.
Figure 5:
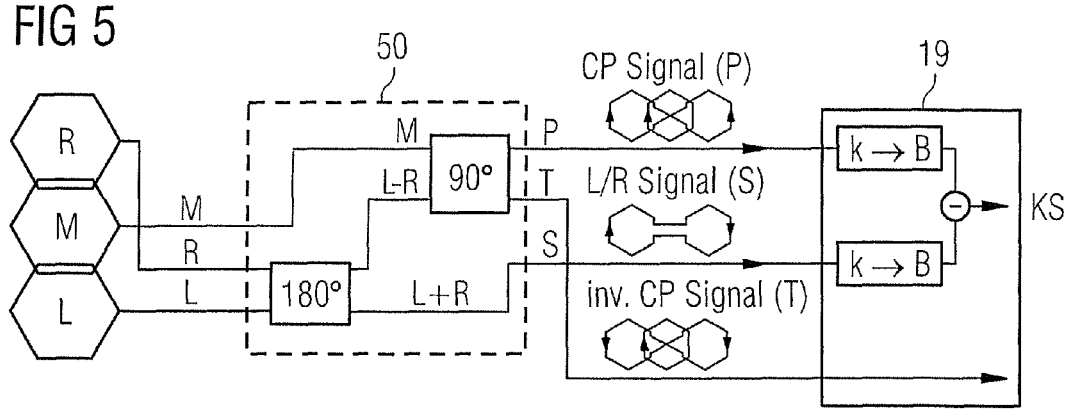
FIG. 5 schematically illustrates the combination of MR signals, wherein the formation of MR mode signals by means of a mode matrix takes place before the combination.
Figure 6:
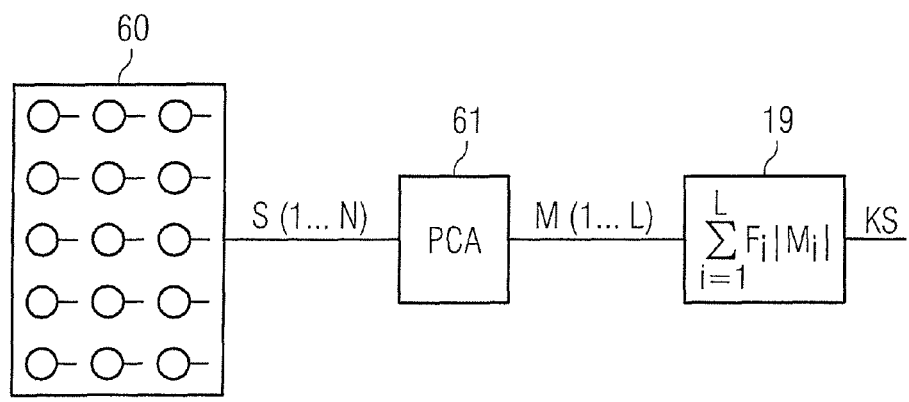
FIG. 6 schematically illustrates the combination of MR signals, wherein a principal component analysis of the MR coil signals acquired with a coil array takes place before the combination.

FIG. 4-6 schematically illustrate possibilities of forming the combined MR signal that can respectively be used in the magnetic resonance system 100 of FIG. 1.

In the example of FIG. 4, the acquisition unit 26 of the magnetic resonance system comprises four acquisition coils that are identified with the numbers 1-4. Given the implementation of an MR sequence, the coils 1-4 detect parallel RF signals from different regions of the examination subject 11.

The induction signals generated by the acquisition coils are demodulated in the acquisition units (identified with reference character 40) and are subsequently converted in the analog-to-digital converter 41 into digital MR coil signals that are identified with S1-S4 in FIG. 1. To form the combined MR signal KS, these are respectively weighted with a weighting factor F1-F4 and added (linear combination) to form the combined MR signal. The weighting factors are set according to the respective application in order to account more or less for specific MR coil signals in the signal KS. In the example of FIG. 3, the signals of the coils 1 and 4 could be suppressed if the region to be shown is covered by the coils 2 and 3. In the example of FIG. 2, the signals of the coils 1 and 4 could be weighted less if the structure to be shown is located below the coils 2 and 3. The weighting factors can thus be set depending on the application case.

The determination of the weighting factors can take place automatically. For example, the structure to be shown can be selected and the weighting factors are subsequently determined such that the selected structure is shown with maximum contrast and the remaining structures are sown with minimal contrast, for example by means of an optimization method. Naturally, additional methods are also conceivable for determination of the weighting factors F1-F4. It should also be clear that more or fewer acquisition coils than shown in FIG. 4 can be provided. It is likewise possible to repeatedly acquire the signals S1-S4 to scan k-space, and to subsequently transform said signals S1-S4 into image space in order to combine the image data obtained in such a manner.

While the acquired MR coil signals are directly provided as MR signals for combination in the example of FIG. 4, in the example of FIG. 5 MR mode signals P, S and T are formed via combination from the MR coil signals (which are identified with the same reference characters) acquired with the acquisition coils R, M and L in the mode matrix 50. The mode matrix 50 can in turn be designed to combine analog coil signals or digital coil signals. In the example of FIG. 5, the formation of the MR mode signals advantageously takes place form analog coil signals. Mode matrix 50 can thus be designed as a hardware element with corresponding circuit components. The primary mode signal P is equivalent to the circularly polarized (CP) signal of what is known as a loop butterfly coil combination. It is formed from the coil signal R, the coil signal L phase-shifted by 180°, and the coil signal M phase-shifted by 90°. The other signals S and T include image information from regions in which the mode signal P does not correspond to the optimal coil weighting. For example, the secondary signal S is formed from the coil signals of the outer coil elements R and L. The tertiary mode signal (T) is the inverse of the primary mode signal P. It should be clear that the mode signals P, S and T can also be formed in the processing unit 19 (instead of in the mode matrix 50), for example in that the individual coil signals R, M and L are supplied in digital form to the processing unit 19 and a combination takes place in digital form.

The mode signals P, S and T can be determined from the coil signals R, M and L by means of the following matrix:

$$\begin{matrix} P \\ S \\ T \end{matrix} = \begin{pmatrix} \frac{1}{2} & \frac{j}{\sqrt{2}} & \frac{1}{2} \\ \frac{1}{\sqrt{2}} & 0 & \frac{1}{\sqrt{2}} \\ \frac{1}{2} & \frac{j}{\sqrt{2}} & \frac{1}{2} \end{pmatrix} \begin{matrix} R \\ M \\ L \end{matrix}$$

Unwanted MR signal portions can subsequently be suppressed via a combination of the mode signals obtained in such a manner in the processing unit 19, wherein the combination takes place according to the respective application.

In the processing unit 19, the provided MR mode signals are initially transformed (k→B) into image space and are subsequently combined again such that the coil signals of the coils that detect unwanted signal portions with increased sensitivity are weighted less. Unwanted signal portions that are caused by bright structures at the edges of the car can be suppressed by a simple subtraction (−) of the magnitude of the transformed mode signal S from the magnitude of the transformed mode signal P, for example. In the example of FIG. 5, the combined MR signal KS is formed by this combination of P and S. It should be clear that the aforementioned mode signals can respectively be an incomplete or complete set of k-space data.

Figure 7:
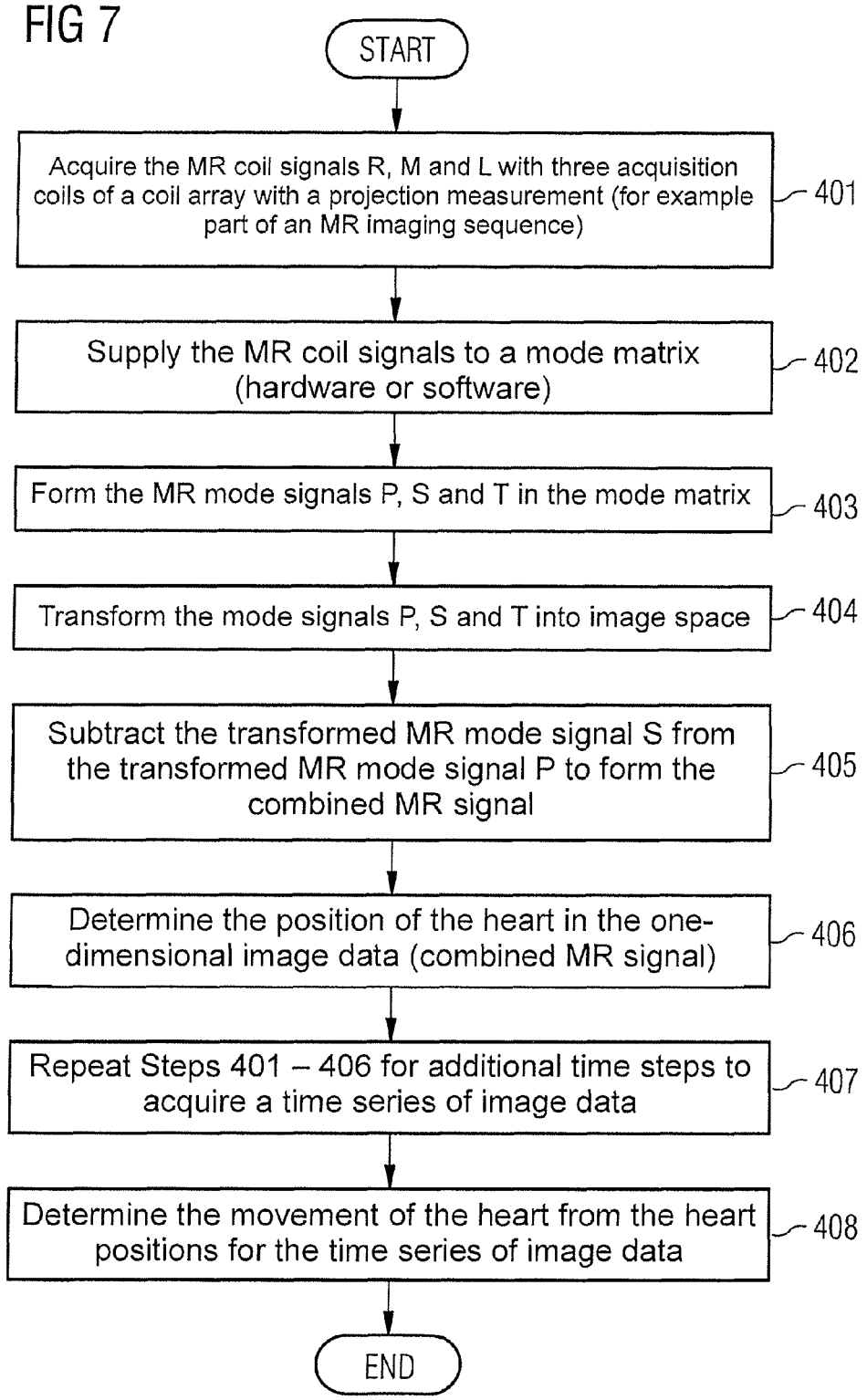
FIG. 7 is a flow chart that illustrates an example of an application according to one embodiment of the method according to the invention.

For example, the method can be used in order to obtain SI projections free of unwanted structures that can be used for a self-triggering given the acquisition of heart image data. The 1D segmentation of the heart is thereby facilitated, and a robust, automatic movement detection is enabled. Such an application is illustrated in the flow diagram of FIG. 7. The method can be implemented in the magnetic resonance system 100 of FIG. 1 with a configuration as shown in FIG. 5.

In a first Step 401, MR coil signals R, M and L are acquired with the three correspondingly named acquisition coils of the coil array with a projection measurement that can also be part of an MR imaging sequence. For example, a projection measurement can take place via the excitation of a volume of the examination subject and acquisition given a frequency coding, whereby the acquired signal represents a projection on the spatial axis in the frequency coding direction.

The acquired coil signals are supplied to the mode matrix 50 in Step 402, wherein these can be implemented as described by means of hardware or software. In the MR mode matrix, the MR mode signals P, S and T are formed in Step 403, for example according to the equation specified above. The formation of the mode signal can take place as described in the publication by A. Reykowski and M. Blasche, "Mode Matrix—A Generalized Signal Combiner For Parallel Imaging Arrays", Proceedings of the 12th Annual Meeting of ISMRM, Kyoto, Japan, 1587 (2004). The MR mode signals formed in such a manner are now supplied to the processing unit 19.

In the present example the acquisition coils R, M and L are positioned over the thorax of an examined person, wherein R and L are arranged over the right or left side of the thorax. The CP mode signal P includes portions of all three coil signals, such that a reconstruction of image data from this signal (given a corresponding scanning of k-space via repeated acquisition of the signal P) leads to the MR image (A) of FIG. 8. Shown in this are essentially all structures within the field of view of the coil array. However, only the heart of the examined subject should be shown for the breath triggering.

For this, in Step 404 the MR mode signals P, S an T are initially transformed into image space. The transformed MR mode signal S is subtracted from the transformed MR mode signal P to form the combined MR signal (KS) (Step 405).

The MR image (B) of FIG. 8 results given a corresponding repeated acquisition of the MR mode signals to scan k-space, transformation of the corresponding k-space data, and what is known as combination. Since the mode signal S essentially contains signal portions from the outer structures of the thorax—for example outer chest wall and arms—these structures are suppressed via subtraction of the transformed signal S from P in the image data. Here a subtraction of the signal magnitudes advantageously takes place. Given a projection of the image on a vertical axis in the image, for example, the position of the heart is thus clearly identifiable.

Since the coil signals were acquired with a projection measurement, a one-dimensional profile results in which the heart is shown with high contrast given a corresponding acquisition sequence. For example, as was described in the preceding an SSFP sequence with large flip angle can be used for this in order to amplify the signal that is caused by the blood present in the heart.

Using the one-dimensional image data—i.e. the intensity profile—the position of the heart can be determined in Step 406. Various methods are conceivable for this, for example the determination of the position of image points above a defined intensity, the adaptation of a curve to the profile, or the implementation of a manual or automatic segmentation.

The repetition of Steps 401-406 can now take place in Step 407 in order to acquire a time series of one-dimensional image data for a number of time steps. It should be clear that a scanning of k-space to determine two-dimensional or three-dimensional image data can likewise take place in each time step, wherein the projection measurement corresponds to the acquisition of a specific k-space line without phase coding, for example.

Since the position of the heart can thus be determined for each time step, the heart movement can be determined (Step 408). A movement correction of the MR data acquired in the time series can thus take place.

FIG. 9 shows an example of profiles of such a time series that are added to one another, wherein the time axis t runs from left to right and wherein the profile axis z runs from top to bottom. In the left image of FIG. 9 the individual profiles were reconstructed from the primary CP signal P. This corresponds to a projection of the left image of FIG. 8 on the axis Z. As is clear, the position of the heart of the examined person can only be identified with difficulty in the profiles. In contrast to this, the profiles of the time series of the right image was determined by forming the combined MR signal KS. Here the heart is shown with markedly higher contrast in comparison to other structures, such that its position can be identified easily and automatically. Reference character 91 labels the position of the aortic arch, reference character 92 labels the position of the heart and reference character 93 labels the position of the liver.

The segmentation of the heart in the 1D projection is hindered due to the unwanted image signal that is caused by the arms and by the outer chest wall in the profiles of the left image. A segmentation of interesting anatomical structures—for example of the heart or the liver—is possible in a significantly simpler manner in the profiles that were determined using the signal combination KS.

The projections shown in FIG. 9 are individual, central, superior-inferior projections that were acquired with a non-selective, three-dimensional, radial and EKG-triggered (electrocardiogram-triggered) MR measurement. Furthermore, in the measurement a saturation slice was positioned in the anterior chest wall, i.e. the chest wall facing towards the coil array. The projections were acquired at 50 successive heart beats.

The stationary signals that are generated by the ribcage and overlap the movement of the heart can thus be effectively suppressed via the application of the embodiment of the method according to the invention. As soon as the heart movement has been determined according to the embodiment, image data can be determined using a corresponding movement correction, wherein a combination for optimally homogeneous illumination of the field of view can hereby be formed in turn so that all structures within the field of view are shown. However, as illustrated in FIG. 8 it is also possible to produce a suppression of the irrelevant structures by means of the described method in the final, movement-corrected depiction.

FIG. 6 illustrates an additional possible configuration of the MR system 100 in which an embodiment of the method according to the invention can be used. The acquisition unit 26 of the MR system 100 includes a coil array 60 that has a plurality of acquisition coils. The coil signals $S (1 \ldots N)$ are acquired with the N acquisition coils, wherein acquisition units are no longer shown in FIG. 6 (just as in FIG. 5). The N coil signals S are subsequently supplied to a PCA unit 61 that produces a principal component analysis of the coil signals. The acquired coil signals are frequently no longer linearly independent of one another, in particular the coil signals of adjacent coils. "Independent coils" that, for example, are determined by a linear combination of the acquisition coils of the coil array can be identified in the coil signals via an principal component analysis. L linearly independent mode signals $M (1 \ldots L)$ can be obtained via a corresponding combination of the coil signals. On the one hand, a reduction of the signal channels to be processed can thus be achieved; on the other hand, any combinations of coil signals can be realized by means of the linearly independent mode signals since these correspond to the principal components.

The mode signals $M (1 \ldots L)$ are provided to the processing unit 19. Processing unit 19 can combine these in k-space or after transformation into image space. The combination of these mode signals takes place again in order to suppress unwanted MR signal portions. This can take place as described in the preceding, for example via linear combination with weighting with the factors $F_i$ ($i=1 \ldots L$). For example, an optimization of the combination of the linearly independent (possibly transformed) mode signals is implemented so that a selected region of the examination subject is imaged and structures outside of the selected region are suppressed. The combination signal KS is now output for additional processing. The mode signals can be acquired repeatedly to scan k-space.

The establishment of the manner in which the MR signals are to be combined in order to obtain the combined MR signal can, for example, be established by means of a reference measurement. The measurement of a phantom can take place, wherein the weighting factors of the combination are subsequently established so that the unwanted signal portions are suppressed. These combination parameters only need to be determined once and can be applied in subsequent measurements to combine the provided MR signals. For example, these same combination factors can be used to determine each of the combined MR signals from which the projection shown in FIG. 9 (right image) were determined. In the example of FIG. 9, the combination factors $F_1$ and $F_2$ for a linear combination of the mode signals P and S amounted to 1 or, respectively, −1.

In addition to the suppression of aliasing artifacts and the imaging of unwanted structures in the image data, additional applications of the methods described in the preceding are also possible. For example, susceptibility artifacts or artifacts caused by magnetic field inhomogeneities can be suppressed. This is possible particularly when the signal portions leading to the artifacts are detected by one or more defined acquisition coils with increased sensitivity. Such artifacts in the combined MR signal can be reduced via lower weighting of the corresponding coil signals or, respectively, signal portions.

The method can be used with the most varied imaging techniques. For example, imaging sequences can be used that scan k-space radially or in a Cartesian manner. Given a radial scan, two- or three-dimensional k-space is scanned along what are known as "spokes" that extend through the center of k-space. Due to the higher scan density in the center of k-space, such acquisition methods are less prone to artifact formation given an undersampling. However, here as well an omission of spokes leads to a reduction of the field of view and thus to aliasings that can be reduced with the methods described in the preceding. An artifact reduction given undersampling can thus be achieved with the most varied scanning methods. The described method is also compatible with accelerated acquisition methods, in particular with partially parallel acquisition methods (PPA methods) such as GRAPPA, SENSE or SMASH, for example.

Features of the embodiments described in the preceding and examples of the invention can naturally be combined.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for combining magnetic resonance (MR) signals, comprising:
providing a computerized processor with at least two MR input signals that are based on MR acquired signals respectively acquired with at least two different acquisition coils of a magnetic resonance imaging system, said at least two MR input signals being selected from the group consisting of respective, individual acquired MR signals and a combination of individual acquired MR signals, said at least two different acquisition coils being located in said magnetic resonance system at respectively different spatial locations, thereby giving said at least two MR input signals respectively different sensitivity profiles; and
providing said computerized processor with a designation of unwanted MR signal portions and, in said computerized processor, automatically suppressing said unwanted MR signal portions by combining said at least two MR input signals with respective weightings that are lower for any of said at least two MR input signals that is based on MR acquired signals acquired with an acquisition coil, among said at least two different acquisition coils, with which said unwanted signal portions were acquired with a higher sensitivity in comparison to MR acquired signals respectively acquired by other coils among said at least two different acquisition coils, in order to generate a combined MR signal, and making said combined MR signal available in electronic form at an output of said computerized processor.

2. A method as claimed in claim 1 comprising weighting said at least two MR input signals with respective weighting factors and, in said computerized processor, automatically adapting the respective weighting factors to minimize a contribution of said unwanted MR signal portions in said combined MR signal.

3. A method as claimed in claim 1 comprising providing said computerized processor with said designation of said unwanted MR signal portions by specifying a region of an examination subject, from which said MR acquired signals are acquired with said at least two different acquisition coils, that is to be shown in image space, and designating said unwanted signal portions as signal portions originating from outside of said region, and applying said lower weighting to at least one of said at least two MR signals based on an MR acquired signal acquired by an acquisition coil at a position that detects MR acquired signals from outside of said region.

4. A method as claimed in claim 1 comprising designating said unwanted signal portions in said computerized processor by entering a designation in said computerized processor selected from the group consisting of a designation of a structure that is to be suppressed in an examination subject from which said MR acquired signals are acquired, and a designation of a field of view with respect to an examination subject from said MR acquired signals are acquired, with said unwanted signal portions being signal portions originating from said designated structure or outside of said field of view.

5. A method as claimed in claim 1 wherein said MR input signals are analog signals, and comprising converting said analog MR input signals in said computerized processor into digital MR input signals, and digitally combining said digital MR input signals.

6. A method as claimed in claim 1 comprising providing said at least two MR input signals to said computerized processor respectively as at least two MR image data sets, each of said at least two MR image data sets representing an MR acquired signal acquired with one of said acquisition coils and transformed into image space, or a combination of MR acquired signals respectively acquired with different acquisition coils and transformed into image space.

7. A method as claimed in claim 1 comprising formulating at least one of said MR input signals as an MR mode signal representing a combination of a plurality of said MR acquired signals.

8. A method as claimed in claim 7 comprising acquiring said MR acquired signals in analog form and combining the analog MR acquired signals to form said MR mode signal.

9. A method as claimed in claim 7 comprising acquiring said MR acquired signals in digital form and combining the digital MR acquired signals to form said MR mode signal.

10. A method as claimed in claim 1 comprising operating on said MR acquired signals to implement a principal component analysis of said MR acquired signals to determine linearly independent principal components of said MR acquired signals, and combining said MR acquired signals, to formulate at least two linearly independent MR mode signals respectively corresponding to the determined principle components, and providing said MR mode signals to said computerized processor as said at least two MR input signals.

11. A method as claimed in claim 10 comprising formulating said at least two linearly independent MR mode signals as a linear combination of at least two MR acquired signals that are respectively weighted with a weighting factor selected from the group consisting of real weighting factors and imaginary weighting factors.

12. A method as claimed in claim 7 wherein said at least two different acquisition coils include a first outer coil, a middle coil, and a second outer coil that respectively detect MR acquired signals RM and L, and comprising formulating a first of said at least two MR mode signals according to $$\frac{1}{2}R$$
$$\frac{i}{\sqrt{2}}M$$
$$\frac{1}{2}L,$$

and formulating a second of said MR mode signals according to $$\frac{1}{\sqrt{2}}R + \frac{1}{\sqrt{2}}L,$$

and forming said combined MR signal by transforming said first and said second of said MR mode signals into image space to obtain first and second transformed MR signals each having a magnitude and subtracting the magnitude of the second transformed MR signal from the magnitude of the first transformed MR signal.

13. A method as claimed in claim 1 comprising employing a coil array that comprises said at least two acquisition coils in said magnetic resonance imaging system.

14. A method as claimed in claim 1 comprising acquiring said MR acquired signals in a reference measurement implemented with said magnetic resonance imaging system.

15. A method as claimed in claim 14 comprising repeatedly acquiring MR acquired signals with said at least two acquisition coils to scan k-space with a k-space scanning trajectory selected from the group consisting of a Cartesian trajectory and a radial trajectory to at least partially fill k-space with k-space data, and reconstructing image data from the k-space data to form said first and second transformed MR signals.

16. A method as claimed in claim 1 comprising acquiring the MR acquired signals with a projection measurement that images a projection of a structure in an examination subject from which the MR acquired signals are acquired, and reconstructing a one-dimensional image from the MR acquired signals, or a combination of the MR acquired signals, and forming said combined MR signal with MR signal portions caused by said structure to be suppressed.

17. A method as claimed in claim 1 comprising combing the MR acquired signals into respective MR image data sets by a repeatedly implemented acquisition procedure to provide a time series of combined image data, and, in said computerized processor, determining movement of an imaged structure in said time series by determining a position of the imaged structure in the image data of the time series.

18. A magnetic resonance (MR) apparatus comprising:
an MR data acquisition device having at least two different acquisition coils at respectively different locations in said data acquisition unit, said at least two different acquisition coils thereby having respectively different sensitivity profiles;
a computerized processor provided with at least two MR input signals that are based on MR acquired signals respectively acquired with said at least two different acquisition coils, said at least two MR input signals being selected from the group consisting of respective, individual acquired MR signals and a combination of individual acquired MR signals; and
said computerized processor being provided with a designation of unwanted MR signal portions and said computerized processor being configured to automatically suppress said unwanted MR signal portions by combining said at least two MR input signals with respective weightings that are lower for any of said at least two MR input signals that is based on MR acquired signals acquired with an acquisition coil, among said at least two different acquisition coils, with which said unwanted signal portions were acquired with a higher sensitivity in comparison to MR acquired signals respectively acquired by other coils among said at least two different acquisition coils, in order to generate a combined MR signal, and to make said combined MR signal available in electronic form at an output of said computerized processor.

19. A non-transitory computer-readable data storage medium encoded with programming instructions, said data storage medium being loadable into a computerized control and processing system of a magnetic resonance imaging system, and said programming instructions causing said control and evaluation system to:
receive as an input at least two MR input signals that are based on MR acquired signals respectively acquired with at least two different acquisition coils of the magnetic resonance imaging system, said at least two MR input signals being selected from the group consisting of respective, individual acquired MR signals and a combination of individual acquired MR signals, said at least two different acquisition coils being located in said magnetic resonance system at respectively different spatial locations, thereby giving said at least two MR input signals respectively different sensitivity profiles; and
receive a designation of unwanted MR signal portions and automatically suppress said unwanted MR signal portions by combining said at least two MR input signals with respective weightings that are lower for any of said at least two MR input signals that is based on MR acquired signals acquired with an acquisition coil, among said at least two different acquisition coils, with which said unwanted signal portions were acquired with a higher sensitivity in comparison to MR acquired signals respectively acquired by other coils among said at least two different acquisition coils, in order to generate a combined MR signal, and make said combined MR signal available in electronic form at an output of said computerized processor.

* * * * *